United States Patent [19]

Rothfuss

[11] 4,289,133
[45] Sep. 15, 1981

[54] CUT-THROUGH BACKUP WASHER FOR THE SCALPEL OF AN INTRALUMENAL SURGICAL STAPLING INSTRUMENT

[75] Inventor: Robert G. Rothfuss, Bellevue, Ky.

[73] Assignee: Senco Products, Inc., Cincinnati, Ohio

[21] Appl. No.: 125,566

[22] Filed: Feb. 28, 1980

[51] Int. Cl.$^3$ .............................................. B31B 1/00
[52] U.S. Cl. ................... 128/334 C; 227/19; 227/DIG. 1
[58] Field of Search ................... 128/305, 334, 334 C; 227/19, DIG. 1, 76

[56] References Cited

U.S. PATENT DOCUMENTS

| 3,193,165 | 7/1965 | Akhalaya et al. | 227/19 |
| 3,388,847 | 6/1968 | Kasulin et al. | 227/19 |
| 3,552,626 | 1/1971 | Astafiev et al. | 227/19 X |

Primary Examiner—Stephen C. Pellegrino
Attorney, Agent, or Firm—Frost & Jacobs

[57] ABSTRACT

A backup washer for the cylindrical scalpel of an intraluminal surgical stapling instrument of the type used to join tubular body organs. The washer comprises an annular member of semi-rigid material having an annular groove formed therein extending from the distal surface of the washer inwardly toward the proximal surface of the washer facing the scalpel. As a result, the washer comprises two spaced annular walls joined at their proximal ends by a thin web providing a backup surface for the scalpel. When the scalpel is advanced by the surgical stapling instrument it will abut and cut through the thin web of the backup washer. When the scalpel cuts through the backup washer web the force required to further advance the scalpel abruptly and noticeably diminishes giving the surgeon clear tactile indication that the surgical staples have been implanted and clinched in the tissue of the tubular body organs being joined and that the scalpel has completely severed the excess tissue.

12 Claims, 11 Drawing Figures

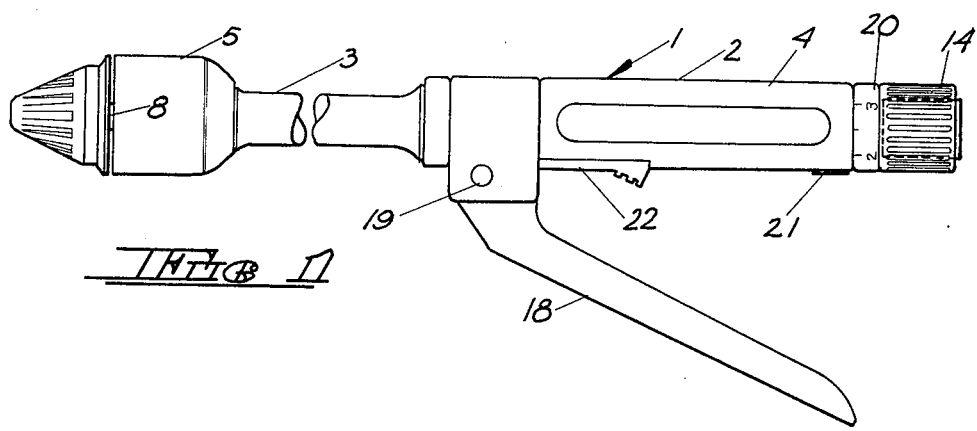
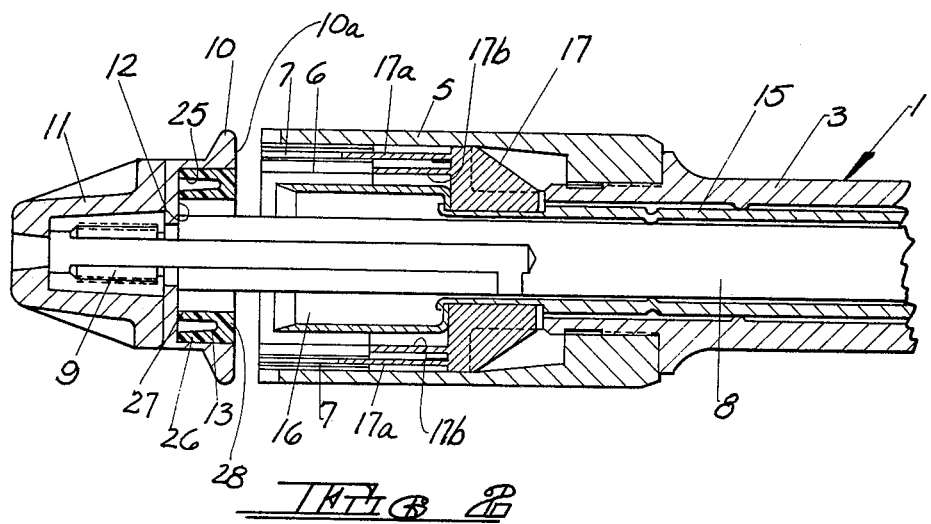

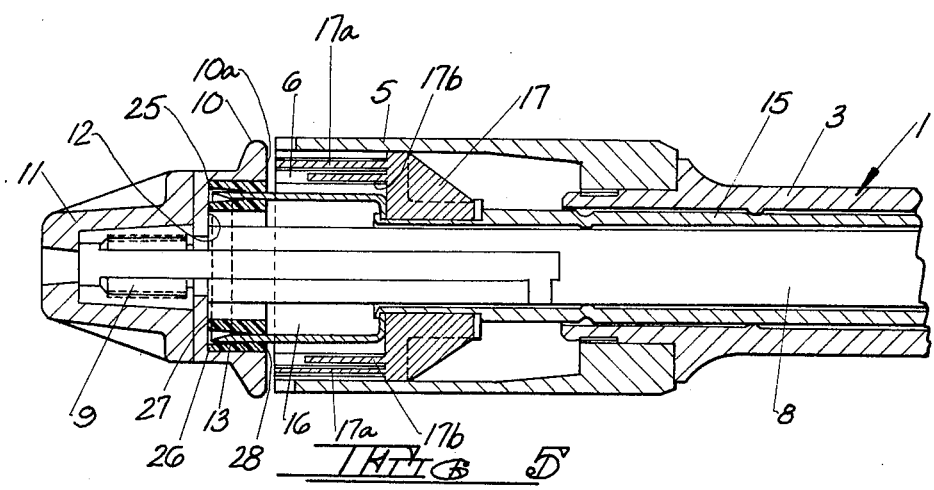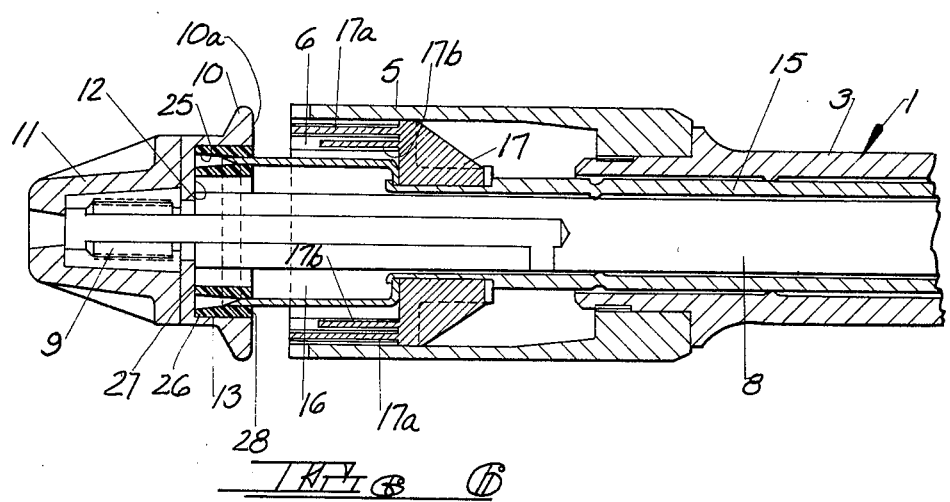

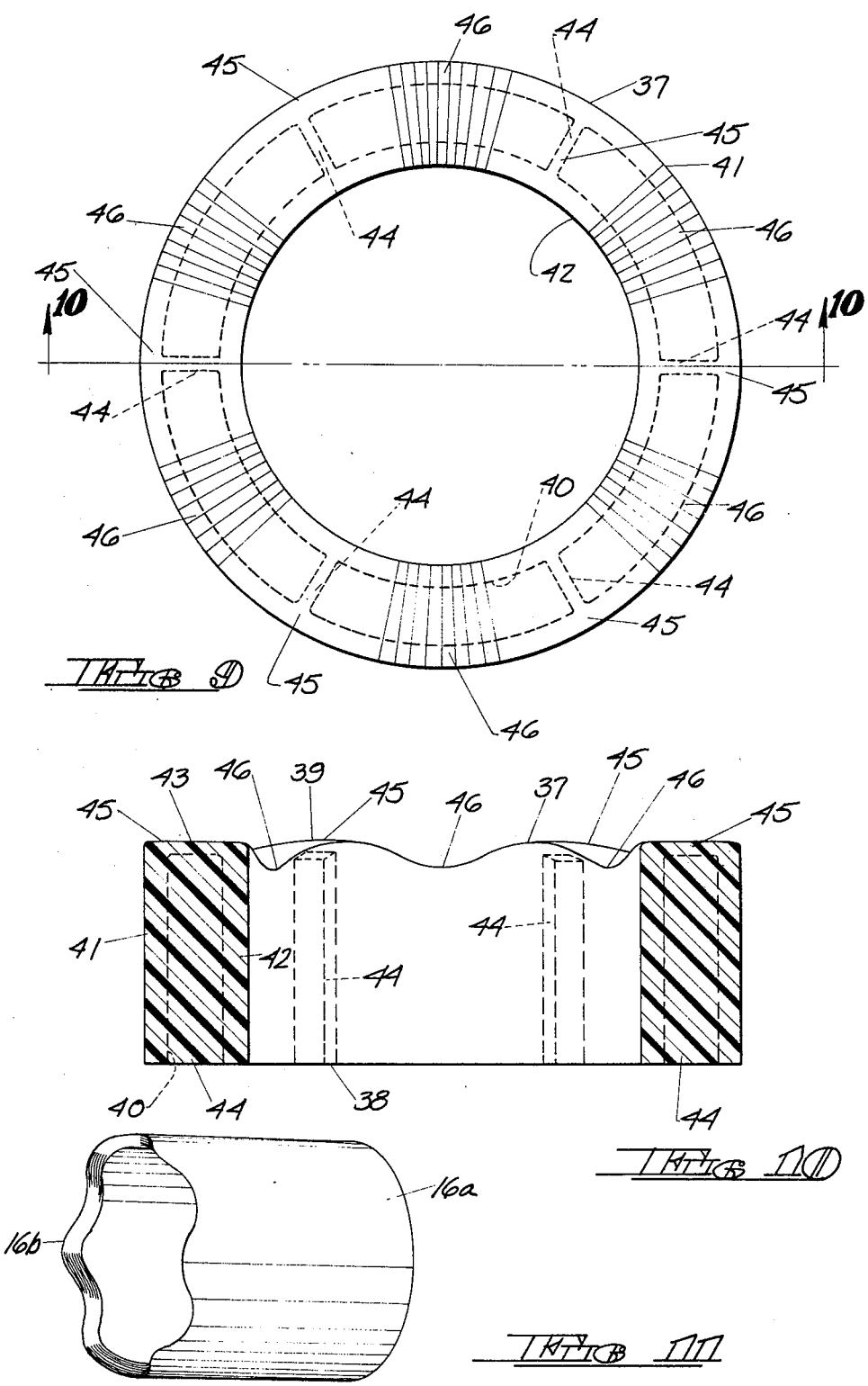

CUT-THROUGH BACKUP WASHER FOR THE SCALPEL OF AN INTRALUMENAL SURGICAL STAPLING INSTRUMENT

TECHNICAL FIELD

The invention relates to a backup washer for the scalpel of an intraluminal surgical stapling instrument, and more particularly to a cut-through backup washer giving the surgeon a clear tactile indication that the stapling and cutting functions of the instrument have been performed.

BACKGROUND ART

While the principles of the present invention can be applied to many types of surgical stapling instruments provided with scalpel means, for purposes of an exemplary showing, the invention will be described in terms of an annular, washer-like backup means for a surgical stapling instrument having a cylindrical scalpel. In recent years there has been an ever increasing use of surgical staples, in lieu of conventional sutures, in many internal organ and intestinal procedures ranging from the esophagus to the rectum. U.S. Pat. Nos. 3,193,165; 3,388,847; 3,552,626, together with copending application Ser. No. 124,954, filed Feb. 26, 1980,; in the name of Robert G. Rothfuss and entitled INTRALUMENAL ANASTOMOSIS SURGICAL STAPLING INSTRUMENT teach exemplary types of surgical stapling instruments devised by prior art workers for such procedures. The use of surgical staples and such surgical stapling instruments has made many difficult procedures much simpler and has significantly reduced the time required for such procedures. This is of importance in that it significantly reduces the length of time for which the patient must be maintained under anesthetic.

Each of the exemplary above mentioned patents and copending application teaches a surgical stapling instrument provided with a cylindrical scalpel and a washer-like backup element for the scalpel made of semi-rigid material. Each of these instruments has a casing or head containing at least one annular array of surgical staples. The cylindrical scalpel and a driver for the surgical staples are normally located within the head. The staple driver and the cylindrical scalpel are actuated by a manually operable lever.

These instruments all have the disadvantage of requiring a high force to embed the cylindrical scalpel into the semi-rigid backup washer. The actual force required is proportional to the depth of penetration of the cylindrical scalpel into the washer. The deeper the scalpel penetrates the washer, the more force is required and this prevents any tactile feed back to the surgeon. As a result, the surgeon never knows from the "feel" of the instrument whether or not the staples have been implanted and clinched or the excess tissue of the tubular organs being joined has been completely excised since the lever of the instrument is usually squeezed to refusal.

The present invention is directed to a cut-through backup washer, the proximal end of which faces the cylindrical scalpel. The cut-through washer comprises inner and outer annular walls joined together at their proximal ends by a thin web providing a backup surface for the cylindrical scalpel. This structure has the advantage that minimal force is used to excise the tissue and as the thin web of the cut-through washer is thereafter severed by the cylindrical scalpel, the force required at the lever of the instrument is abruptly reduced. This abrupt reduction of lever force gives the surgeon a clear and unmistakable tactile signal that the surgical staples have been formed and that the excess tissue of the tubular body organs being joined has been excised by the cylindrical scalpel. Thus, in addition to this tactile signal, the backup washer of the present invention reduces the peak force and work required for the tissue cutting portion of the anastomotic procedure.

The above mentioned copending application teaches an intraluminal anastomosis surgical stapling instrument which will adequately and reliably clinch surgical staples of a predetermined leg length over a working gap between the staple containing casing and the anvil of at least two millimeters. The cut-through backup washer of the present invention is particularly advantageous in such a surgical stapling instrument since the depth of penetration of the backup washer by the cylindrical scalpel required particularly at the minimum end of the working gap of the instrument is considerable. This, in turn, would require considerable force at the lever of the instrument. When this instrument is provided with the cut-through backup washer of the present invention the force required at the lever is greatly reduced and is the same throughout the working gap of the instrument, as will be described hereinafter.

DISCLOSURE OF THE INVENTION

According to the invention there is provided a backup washer for the cylindrical scalpel of an intraluminal surgical stapling instrument of the type used to join tubular body organs. The washer comprises an annular member of semi-rigid material having distal and proximal ends. An annular groove is formed in the washer extending from the annular distal end of the washer inwardly toward the annular proximal end of the washer which faces the scalpel. The resulting structure comprises inner and outer spaced annular walls joined at their proximal ends by a thin web. The web forms a backup surface of the washer for the scalpel. When the scalpel is advanced by the surgical stapling instrument it will abut and cut through the thin web of the backup washer at which point the force required to further advance the scalpel abruptly and noticeably diminishes giving the surgeon a clear tactile signal that the surgical staples have been implanted and clinched in the tissue of the tubular body organs being joined and that the scalpel has severed the excess tissue.

In a second embodiment of the present invention the annular groove or recess in the backup washer is of greater width, thereby reducing the thickness of the inner and outer walls of the washer and increasing the width of the thin web joining their proximal ends. The inner and outer walls are additionally joined by a plurality of thin, radially oriented, stiffening webs equally spaced from each other about the inner and outer walls. The stiffening webs are perpendicular to and are joined to the thin web connecting the proximal ends of the inner and outer walls. This second embodiment of the backup washer functions in the same manner as the first embodiment with the exception that the washer of the second embodiment is never completely severed by virtue of the stiffening webs and its tactile signal is slightly less than that of the first embodiment, again by virtue of the stiffening webs. On the other hand, the greater width of the thin web joining the proximal ends of the inner and outer walls provides a wider backup surface for the cylindrical scalpel and thus allows for greater non-concentricity of the cylindrical scalpel.

Either the first or the second embodiment could be modified by configuring the proximal ends of the inner and outer walls and the thin web joining them so that they have an undulating shape. This would reduce the force required to sever the web joining the proximal ends of the inner and outer walls. As the cylindrical scalpel contacts the undulated surface of the web, it in effect produces a slicing action since it first cuts the peaks of the undulated web and thereafter the valleys, rather than cutting through all of the web simultaneously. A similar effect can be achieved with the first or second embodiment of the present invention by providing a cylindrical scalpel having an undulated cutting edges.

BRIEF DESCRIPTION OF THE DRAWINGS

FIG. 1 is a fragmentary side elevational view of an exemplary intraluminal anastomosis surgical stapling instrument to which the teachings of the present invention can be applied.

FIG. 2 is a fragmentary cross sectional view of the distal end of the instrument of FIG. 1, illustrating the staple containing casing with the staple driver and cylindrical scalpel therein and an anvil provided with a backup washer of the present invention.

FIG. 5 is a fragmentary cross sectional view similar to FIG. 2, illustrating the cylindrical scalpel in its forwardmost position when the surgical stapling instrument is set at the minimum of its working gap.

FIG. 6 is a fragmentary cross sectional view similar to FIG. 5 and illustrating the cylindrical scalpel in its forwardmost position with the instrument set at the maximum of its working gap.

FIG. 9 is a top plan view of another embodiment of the washer of the present invention.

FIG. 10 is a cross sectional view taken along section line 10—10 of FIG. 9.

FIG. 11 is a perspective view of a modified form of a cylindrical scalpel.

BEST MODE OF CARRYING OUT THE INVENTION

Figure 3:
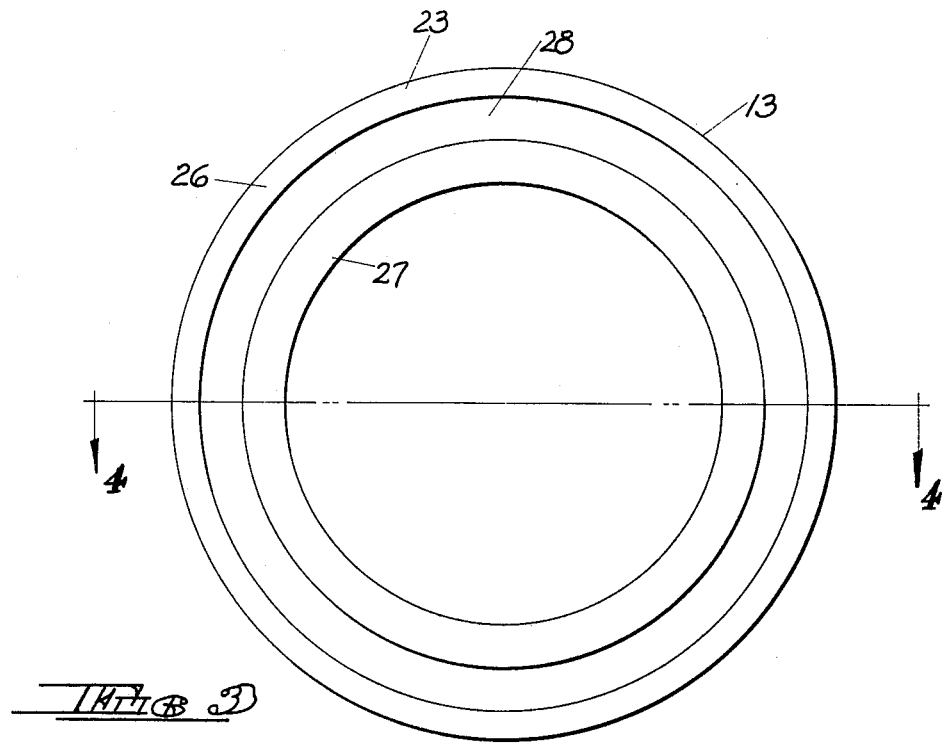
FIG. 3 is an elevational view of the distal end of the backup washer of the present invention.

While the present invention may be applied to many types of surgical stapling instruments employing scalpel means, for purposes of an exemplary showing it will be described in its application to the surgical stapling instrument of the above mentioned copending application Ser. No. 124,954, filed Feb. 26, 1980, in the name of Robert G. Rothfuss and entitled INTRALUMINAL ANASTOMOSIS SURGICAL STAPLING INSTRUMENT.

Such an instrument is illustrated in FIGS. 1 and 2 wherein like parts have been given like index numerals. The instrument is generally indicated at 1 and comprises an elongated body 2 having a tubular housing portion 3 and a coaxial cylindrical handle portion 4 of slightly larger diameter. At the distal end of tubular housing portion 3 there is mounted a cylindrical casing 5. The casing 5 contains near its distal end an annular staple guide 6. The staple guide 6 supports one or more annular arrays of surgical staples. The embodiment illustrated contains two concentric annular staple arrays, two staples of the first array being shown at 7, the staples of the second array not being visible in FIGS. 1 and 2.

Extending axially and longitudinally of the body 2 there is an adjusting rod 8. The distal end 9 of adjusting rod 8 extends beyond casing 5 and has an anvil member 10 affixed thereto by an anvil nut 11. The anvil 10 is of button-like cross section (as shown in FIG. 2) and has a central depression 12 in which a washer 13 of the present invention is mounted.

Adjusting rod 8 has a threaded portion (not shown) threadedly engaged with an adjustment nut 14 rotatively mounted at the proximal end of instrument body 2. Rotation of adjustment nut 14 results in axial shifting of adjusting rod 8 so that the anvil surface 10a of anvil 10, facing the distal end of casing 5, can be shifted between a position adjacent casing 5 and a position spaced from casing 5.

Mounted on adjusting rod 8 there is a cylindrical, hollow driver tube 15. The distal end of driver tube 15 mounts a cylindrical scalpel 16 and a staple driver 17. Staple driver 17 has a tang for each surgical staple 7 of the first array by which, when the driver 17 is actuated, the surgical staples 7 are driven through the tissue of the tubular body organs to be joined and are thereafter clinched against anvil surface 10a. Two such tangs are shown at 17a. The driver 17 also has a second set of tangs serving the same purpose as tangs 17a for the surgical staples of the second array (not shown). To such tangs are shown at 17b.

The staple driver 17 and cylindrical scalpel 16 are shiftable between a retracted position shown in FIG. 2 and an actuated position shown in FIGS. 5 and 6 by driver tube 15. Driver tube 15, in turn, is axially shiftable by a lever 18 pivotally mounted to the instrument body 2 by a pivot pin 19. The proximal end of driver tube 15 (not shown) is operatively connected to lever 18 so that when lever 18 is shifted from its normal position as shown in FIG. 1 toward instrument body 2, the driver tube 15 will cause cylindrical scalpel 16 and staple driver 17 to shift from their retracted positions to their actuated positions. A means (not shown) is also provided to bias lever 18 to its normal position as shown in FIG. 1, thus biasing cylindrical scalpel 16 and staple driver 17 to their retracted positions.

The instrument 1 is designed to adequately drive and clinch surgical staples of a single predetermined leg length over a range of distances between anvil surface 10a and the distal end of casing 5, termed the "working gap" of the instrument. The instrument is capable of placing "end-to-end", "end-to-side", "side-to-side" and "side-to-end" anastomoses. For example, in a simple "end-to-end" anastomosis of two tubular body organs or lumens, the distal end of the instrument 1 is inserted into a first one of the lumens through a natural opening in the patient's body, if possible, or through an incision made in the side of the lumen remote from the anastomotic site. Thereafter, by means of adjustment knob 14, the anvil 10 is shifted away from casing 5, exposing a portion of adjusting rod 8 therebetween. The second lumen is pulled over the anvil 10 and both lumens are tied to the exposed portion of adjusting rod 8 by simple purse string sutures or the like.

Thereafter, by means of adjustment knob 14, the anvil 10 is shifted toward casing 5 until the maximum working gap of the instrument is reached. Then, a final adjustment of the distance between anvil surface 10a and casing 5, within the working gap, is made in accordance with the thickness of the tissues of the lumens being joined. A determination of the tissue thickness can be made, for example, by use of an appropriate instrument such as that taught in copending application Ser. No. 124,954, filed Feb. 26, 1980, in the names of Robert G. Rothfuss and Edwin L. Stith, Jr., and entitled SURGICAL TISSUE THICKNESS MEASURING INSTRUMENT. To enable this final adjustment, adjustment knob 14 is provided with a ring scale 20 and the proximal end of instrument body 2 is provided with a cooperating index mark 21.

Once the final gap adjustment has been made, the surgical staples can be implanted. Lever 18 may be provided with a safety slide lockout 22, which at this point is shifted to its release position. Lever 18 is then squeezed by the surgeon toward the instrument body 2. This causes staple driver 17 to implant a double annular row of surgical staples in the tubular body organs or lumens being joined, which staples are clinched against anvil forming pockets in anvil surface 10a. This same movement of lever 18 causes cylindrical scalpel 16 to sever from the lumens being joined those excess tissue portions which were tied to adjusting rod 8. During the tissue cutting portion of the anastomotic procedure, the cylindrical scalpel 16 passes through the tissue being cut and abuts and enters backup washer 13. Heretofore, the backup washer has comprised an annular member of semi-rigid material into which the cylindrical scalpel was imbedded. The surgeon simply squeezed lever 18 until it would pivot no further, assuming that the staples had been clinched and that the excess tissue had been excised by cylindrical scalpel 16.

At this point, by means of adjustment knob 14, anvil 10 is shifted away from casing 5 and the instrument is removed from the anastomotic site. The excised tissue is withdrawn with the instrument and the anastomosis procedure is complete.

Figure 4:
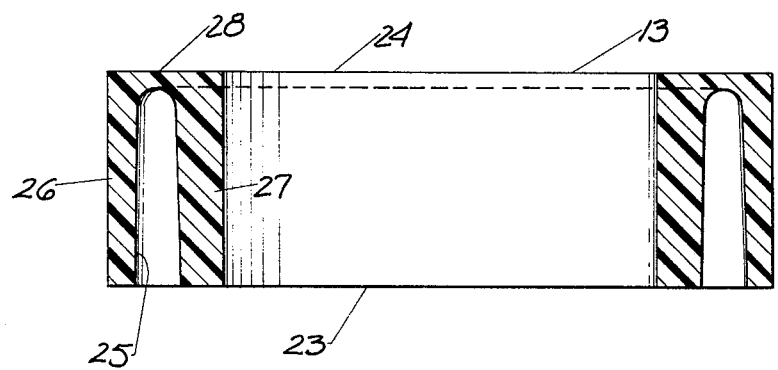
FIG. 4 is a cross sectional view taken along section line 4—4 of FIG. 3.

The improved backup washer 13 of the present invention is shown in FIGS. 3 and 4. The backup washer 13 is formed in any appropriate way of any semi-rigid material suitable for use in a surgical environment and capable of being sterilized without degradation by one or more of the well known standard methods such as autoclave, ethylene oxide, irradiation or the like. While not intended to be so limited, excellent results have been achieved when the washer 13 was molded of polyethylene or polypropylene.

The washer 13 is an annular structure having a distal end 23 and a proximal end 24 adapted to face the distal end of casing 5 of the instrument 1. An annular notch or groove 25 extends inwardly of the washer from its distal end 23 toward, but short of, its proximal end 24. As a result of notch or groove 25 the washer comprises an outer annular wall 26 and an inner annular wall 27 joined at their proximal ends by a thin web 28. The web 28 provides a backup surface for scalpel 16. In most applications, web 28 preferably has a thickness of from about 0.010 inch to about 0.015 inch when washer 13 is made of plastic material such as polyethylene or polypropylene. The thickness of web 28 for best results, will, of course, vary depending upon the material from which washer 13 is molded or formed.

FIGS. 2, 5 and 6 illustrate the washer 13 mounted in the anvil 10 of instrument 1. During the cutting portion of the anastomotic procedure, the scalpel 16, using washer 13 as a backup, will cut through the excess tissue of the lumens being joined and next will abut and begin to penetrate web 28. As soon as web 28 has been penetrated, the force required at lever 18 to further advance scalpel 16 will abruptly and noticeably diminish. This abrupt change in the force required at lever 18 constitutes a clear tactile signal to the surgeon that the staples have been implanted and clinched by driver 17 and that the excess tissue has been excised by cylindrical scalpel 16. FIG. 5 illustrates scalpel 16 in its forwardmost position when the instrument 1 has been set at the minimum of its working gap. FIG. 6 shows the scalpel 16 in its forwardmost position when the instrument 1 has been set at the maximum of its working gap. It will be evident from FIGS. 5 and 6 that in the instance of a typical prior art solid backup washer of semi-rigid material, considerable penetration of such a washer is required even when the instrument 1 is set at the maximum of its working gap and particularly when the instrument is set at a gap less than the maximum of its working gap. The force to penetrate a solid backup washer of semi-rigid material is proportional to the depth of penetration of the cylindrical scalpel 16 into the washer and with the use of prior art washers no tactile signal was given to the surgeon that the instrument had performed its function. With the use of backup washer 13, not only is the above noted tactile signal imparted to the surgeon, but also the tissue cutting force required to actuate lever 18 is independent of the gap setting, being simply that required to penetrate backup washer web 28.

When backup washer 13 of FIGS. 3 and 4 is molded of a plastic material, those surfaces of walls 26 and 27 facing the groove or notch 25 may be slightly tapered such that notch 25 is slightly wider at the distal surface 23 of the washer to assist in release of washer 13 from the mold.

Figure 7:
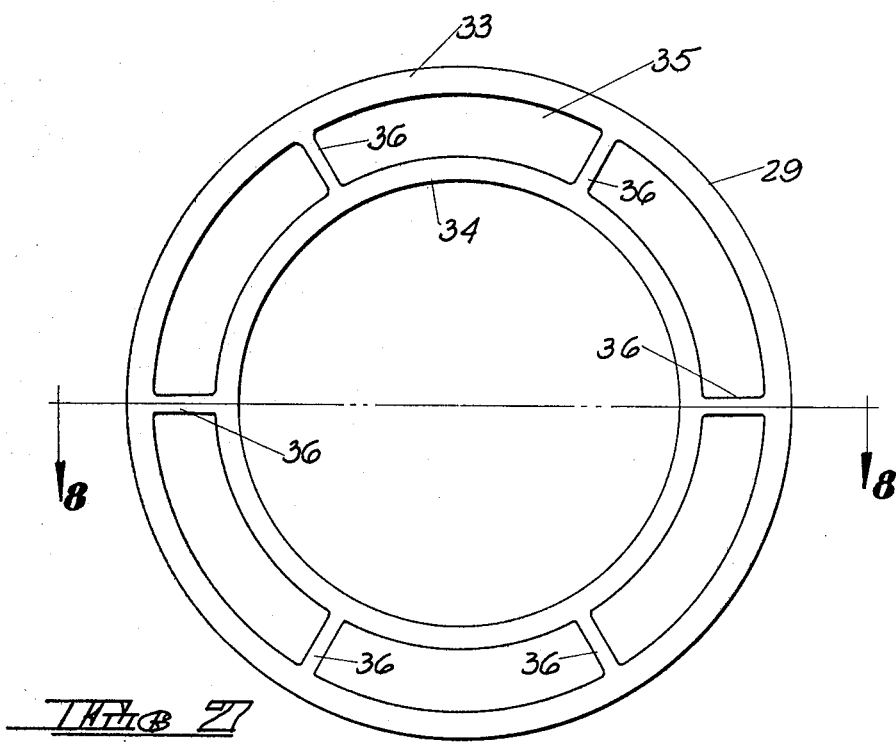
FIG. 7 is an elevational view of the distal end of a second embodiment of the washer of the present invention.
Figure 8:
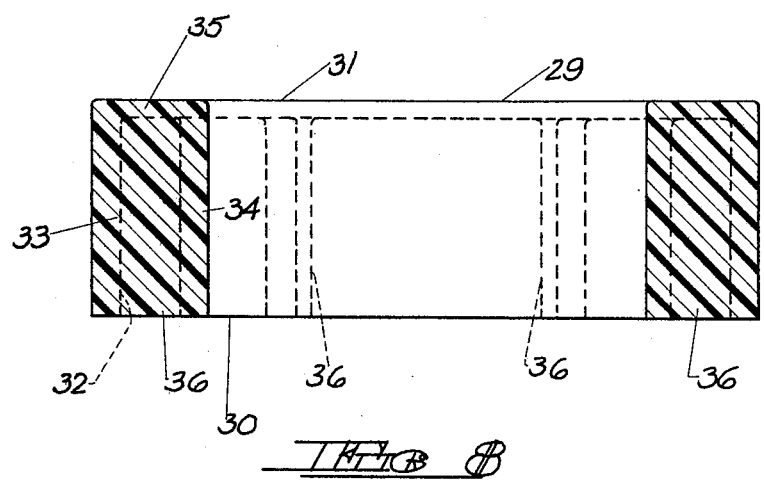
FIG. 8 is a cross sectional view taken along section lines 8—8 of FIG. 7.

A second embodiment of the backup washer of the present invention is illustrated in FIGS. 7 and 8, wherein like parts have been given like index numerals. In this embodiment, the backup washer is designated by index numeral 29. Washer 29 is an annular member having a distal annular end 30 and a proximal annular end 31. Once again, the washer is provided with an annular groove or notch 32 which extends from the distal end 30 toward but just short of proximal end 31. The notch or groove 32 forms an outer annular wall 33 and an inner annular wall 34.

The washer 29 of FIGS. 7 and 8 differs from washer 13 of FIGS. 3 and 4 in that the notch or groove 32 is wider than the notch or groove 25. This results in a web 35 connecting the proximal ends of outer wall 33 and inner wall 34 which is of greater width than web 28 of FIGS. 3 and 4. Washer 29 is also provided with a plurality of evenly spaced, radially oriented stiffening webs 36 which are integral with outer wall 33, inner wall 34 and web 35. The washer 29 of FIGS. 7 and 8 may be molded or otherwise formed of any appropriate material as described with respect to the washer 13 of FIGS. 3 and 4. The functioning of backup washer 29 of FIGS. 7 and 8 is identical to that described with respect to backup washer 13 of FIGS. 3 and 4 with the following exceptions. The greater width of annular web 35 joining outer wall 33 and inner wall 34 provides a wider backup surface for cylindrical scalpel 16 and therefore permits greater non-concentricity of cylindrical scalpel 16. The diminishing of the force at lever 18 at the instant scalpel 16 cuts through web 35 will not be quite as abrupt by virtue of stiffening webs 36. Nevertheless, it will be more than adequate to give a clear and unmistakable tactile signal to the surgeon. Finally, washer 29 of FIGS. 7 and 8 will never be severed into two separate pieces as will washer 13 of FIGS. 3 and 4. This is true because even at the minimum of the instrument working gap, the radial stiffening webs 36 will not be completely severed.

Yet another embodiment of the washer of the present invention is shown in FIGS. 9 and 10, wherein like parts have again been given like index numerals. In FIGS. 9 and 10 the washer is indicated by index numeral 37 and constitutes an annular member having an annular distal end 38 and an annular proximal end 39, intended to face casing 5 of the instrument 1. Washer 37 is similar to washer 29 in that it is provided with a large internal notch or groove 40 similar to notch or groove 32 of washer 29. Notch or groove 40 forms an outer wall 41, an inner wall 42 and a thin connecting web 43. As in the case of washer 29 of FIGS. 7 and 8, the washer 37 is provided with a plurality of evenly spaced, radially oriented stiffening webs 44.

The washer 37 differs from washer 29 of FIGS. 7 and 8 only in that its proximal end 39 (made up of the proximal ends of outer wall 41 and inner wall 42 and connecting web 43) is undulated as shown. The undulated proximal end 39 has a series of regularly spaced peaks 45 and a series of regularly valleys 46.

Washer 37 functions in the same manner described with respect to washer 29 of FIGS. 7 and 8 with the exception that during the cutting portion of the anastomotic procedure, cylindrical scalpel 16 first contacts and cuts the peaks 45 of web 43, thereafter cutting through the valleys 46. Since cylindrical scalpel 16 does not cut through all of web 43 simultaneously, the cutting force to sever web 43 is reduced and cutting action of cylindrical scalpel 16 is in effect a slicing action.

It will be understood by one skilled in the art that the washer 13 of FIGS. 3 and 4 could similarly be provided with an undulated proximal end 24 and web 28. Furthermore, a similar slicing action can be achieved with washer 13 of FIGS. 3 and 4 and washer 29 of FIGS. 7 and 8, both having planar proximal ends 24 and 31, respectively, if the cylindrical scalpel 16 were, itself, provided with an undulated cutting edge. Such a cylindrical scalpel is shown at 16a in FIG. 11, having an undulated cutting edge 16b.

All of the embodiments of the backup washer of the present invention reduce the peak force and work required for the tissue cutting portion of an anastomotic procedure. All of them provide a tactile feedback or signal to the surgeon that the surgical staples are implanted and clinched and that the excess tissue has been excised by cylindrical scalpel 16. The washers of the present invention make more practical the provision of an intraluminal surgical stapling instrument having a working gap constituting a range of distances between anvil surface 10a and casing 5 over which surgical staples of a predetermined leg length can be adequately clinched. By providing the washers with an undulated proximal end and inner and outer wall connecting web, the force required to sever the web is reduced since the cutting action of the cylindrical scalpel is, in effect, a slicing action.

Modifications may be made in the invention without departing from the spirit of it.

What is claimed is:

1. In a surgical stapling instrument having a scalpel; the improvement comprising: a backup member for said scalpel, said backup member having a pair of parallel spaced walls, said walls having corresponding edges, said corresponding edges being joined by a thin web, said web providing a backup surface for said scalpel severable by said scalpel, said walls and web constituting an integral, one piece structure of semi-rigid material.

2. In a surgical stapling instrument having a cylindrical scalpel; the improvement comprising: a backup washer for said cylindrical scalpel, said washer including an annular member of semi-rigid material having an annular distal end and an annular proximal end facing said scalpel, said washer having a cylindrical outer wall and a concentric cylindrical inner wall spaced from said outer wall, a thin web at said proximal end of said washer joining said inner and outer walls, said web providing a backup surface for said scalpel and being severable thereby.

3. The structure claimed in claim 2 wherein said web is planar, said cylindrical scalpel of said instrument having an undulated cutting edge.

4. The structure claimed in claim 2 including a plurality of evenly spaced and radially oriented stiffening webs extending between said inner and outer walls.

5. The structure claimed in claim 4 wherein said backup washer comprises an integral one piece molded member.

6. The structure claimed in claim 5 wherein said backup washer is molded of plastic material chosen from the class consisting of polyethylene and polypropylene.

7. The structure claimed in claim 6 wherein said web joining said inner and outer walls at said proximal end of said washer is from about 0.010 to about 0.015 inch thick.

8. The structure claimed in claim 2 wherein said proximal end of said backup washer including said web is regularly undulated.

9. The structure claimed in claim 8 including a plurality of evenly spaced and radially oriented stiffening webs extending between said inner and outer walls.

10. The structure claimed in claim 2 wherein said backup washer comprises an integral one piece molded member.

11. The structure claimed in claim 10 wherein said backup washer is molded of plastic material chosen from the class consisting of polyethylene and polypropylene.

12. The structure claimed in claim 11 wherein said web joining said inner and outer walls at said proximal end of said washer is from about 0.010 to about 0.015 inch thick.

* * * * *